United States Patent
Propp

(10) Patent No.: US 6,364,832 B1
(45) Date of Patent: Apr. 2, 2002

(54) VAGINAL LATERAL WALLS RETRACTOR FOR USE IN COMBINATION WITH VAGINAL SPECULA AND METHOD OF PERFORMING VAGINAL/CERVICAL EXAMINATION

(75) Inventor: Donald J. Propp, Dewitt, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 0 days.

(21) Appl. No.: 09/558,252

(22) Filed: Apr. 25, 2000

Related U.S. Application Data
(60) Provisional application No. 60/173,010, filed on Dec. 23, 1999.

(51) Int. Cl.[7] .................................................. A61B 1/32
(52) U.S. Cl. ...................... 600/220; 600/208; 600/219; 600/235; 600/245; 600/201
(58) Field of Search ...................... 600/184, 201, 600/208, 210, 205, 220, 219, 221, 222, 223, 235, 245, 224; 606/119

(56) References Cited

U.S. PATENT DOCUMENTS

| | | | | |
|---|---|---|---|---|
| 1,020,281 A | * | 3/1912 | Hall | |
| 2,406,600 A | * | 8/1946 | Forestiere | 600/184 |
| 3,192,928 A | * | 7/1965 | Horton | |
| 3,581,738 A | * | 6/1971 | Moore | |
| 3,774,596 A | * | 11/1973 | Cook | 600/184 |
| 5,165,387 A | * | 11/1992 | Woodson | |
| 5,743,852 A | * | 4/1998 | Johnson | 600/207 |
| 5,846,249 A | * | 12/1998 | Thompson | 606/119 |
| 6,036,638 A | * | 3/2000 | Nwawka | 600/186 |
| 6,096,047 A | * | 8/2000 | Smit | 606/119 |

OTHER PUBLICATIONS

"New Vaginal Speculum", The Lancet, Jun. 25, 1960, p. 1392.*

* cited by examiner

Primary Examiner—Jeffrey A. Smith
(74) Attorney, Agent, or Firm—Fildes & Outland, P.C.

(57) ABSTRACT

A vaginal lateral walls retractor for use with a vaginal speculum to retract the vaginal lateral walls during vaginal/cervical examinations includes a generally tubular sleeve having cross-sectional dimensions that allow the sleeve to fit in between blades of the speculum while the blades are inserted and opened within a vagina. The sleeve retracts the vaginal lateral walls that have pushed in under the inserted and opened speculum blades. The cross-sectional dimension also provides an inside working area for examination and sampling of the vagina and cervix area.

16 Claims, 2 Drawing Sheets

VAGINAL LATERAL WALLS RETRACTOR FOR USE IN COMBINATION WITH VAGINAL SPECULA AND METHOD OF PERFORMING VAGINAL/CERVICAL EXAMINATION

CROSS REFERENCE TO RELATED APPLICATIONS

This application claims the benefit of U.S. Provisional Application No. 60/173,010, filed Dec. 23, 1999.

TECHNICAL FIELD

This invention relates to the performing of vaginal and cervical examinations and more particularly to an apparatus to be used in combination with a vaginal speculum to retract vaginal lateral walls during a vaginal examination.

BACKGROUND OF THE INVENTION

It is known in the art relating to vaginal and cervical examinations to use a vaginal speculum to enlarge the passage through the vagina for gynecological examination, sampling or treatment. Problems arise when conducting visual vaginal and cervical examinations with a conventional two-bladed vaginal speculum on women who are obese, elderly, have excess adipose vaginal tissue, or otherwise poorly toned vaginal walls.

It is often impossible to obtain a complete view of the cervical area and/or impossible to collect valid PAP smear samples because the vaginal walls' excess or relaxed tissue structure of the lateral vaginal walls pushes back in under the speculum blades after the speculum is opened. To overcome this problem, the clinician usually has to insert a pair of metal, surgical, lateral wall retractors inside of the opened speculum. These lateral retractors are expensive and clumsy, and thus nonconducive to single patient use and sampling.

Several other techniques have been unsuccessfully used to solve this problem. For example, condoms or portions of surgeon gloves have been placed over the closed speculum blades before insertion into the vagina. Unfortunately, the condom often simply rolls or slides up the blades during insertion, bunching up, rendering it useless. Further, the condom usually does not have enough force, when the blades are opened, to hold back the vaginal lateral walls. Furthermore, the condom may slip off when the blades are being removed and be left behind in the vagina. Therefore, there is a need for a device that can be used with a vaginal speculum to retract the vaginal lateral walls and which is also disposable, reliable, and cost effective.

SUMMARY OF THE INVENTION

The present invention provides a vaginal lateral walls retractor for use with a two-bladed vaginal speculum during vaginal or cervical examinations. The walls retractor includes a generally tubular sleeve that has cross-sectional dimensions that allow the sleeve to fit between the blades of the speculum while the blades are inserted and opened within the vagina. The sleeve retracts the vaginal lateral walls that have pushed in under the inserted and opened speculum blades. The cross section also provides an inside working area for examination and sampling of the vagina and cervix area.

In one embodiment of the present invention, the sleeve has a length that is about 60% of the length of a blade of the speculum. A handle extends from one end of the sleeve for manipulation by a health care provider. The handle has a length that allows full placement of the sleeve down to and around an outer diameter of the pendulous cervix and allows the sleeve to be pushed toward and away from anterior and posterior vaginal fornix and allows rotation of the sleeve inside the speculum blades.

In another embodiment, the cross section is of a generally rectangular shape with rounded corners. The sleeve has four sides and may have two cutouts on opposing sides at a proximal end of the sleeve so that an ectocervical scraper lobe will not hit the end of the sleeve. The cutouts may be of a generally elliptical shape. The sleeve may include a notch to accommodate a light pipe channel on a disposable speculum. The sleeve may be made of a plastic or metal material.

The present invention also provides an enhanced method of performing a vaginal or cervical examination on a patient. Thereby, blades of a vaginal speculum are inserted into a vagina. Once they are inserted, the blades are opened. Next, a vaginal lateral walls retractor defined by a generally tubular sleeve is inserted in between the opened speculum blades for retracting the vaginal lateral walls. To gain additional wall retraction, the vaginal lateral walls retractor sleeve is of an elongated rectangular shape. The rectangular sleeve is inserted with its longest cross-sectional dimension between the speculum blades and then rotated 90 degrees. Finally, the vaginal and cervical areas are examined and samples may be taken or treatment given.

These and other features and advantages of the invention will be more fully understood from the following detailed description of the invention taken together with the accompanying drawings.

DETAILED DESCRIPTION OF THE INVENTION

Figure 1:
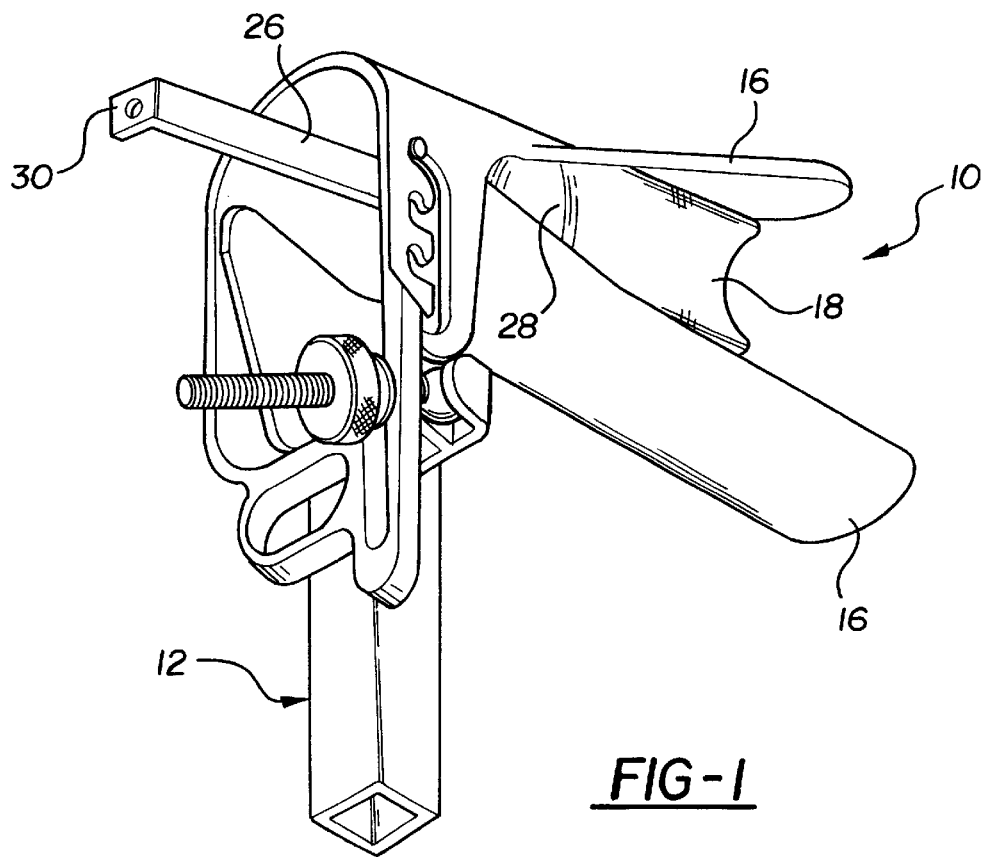
FIG. 1 is perspective view of a vaginal lateral walls retractor and a vaginal speculum in accordance with one embodiment of the present invention.
Figure 2:
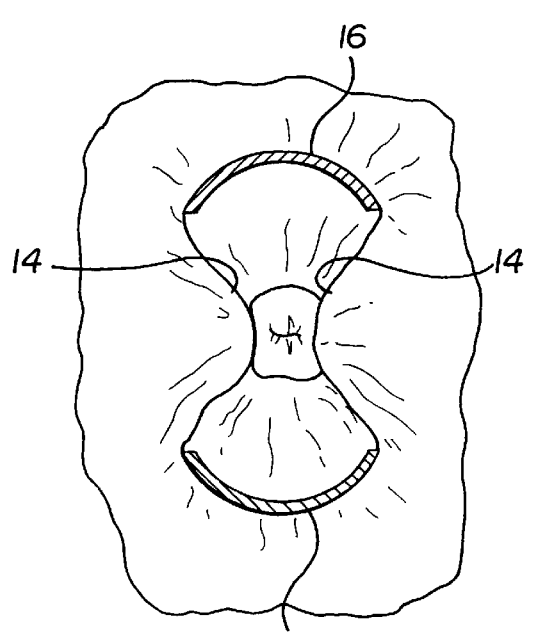
FIG. 2 is a cross-sectional view of blades of the vaginal speculum opened and inserted in a vagina illustrating inwardly extending lateral vaginal walls.
Figure 3:
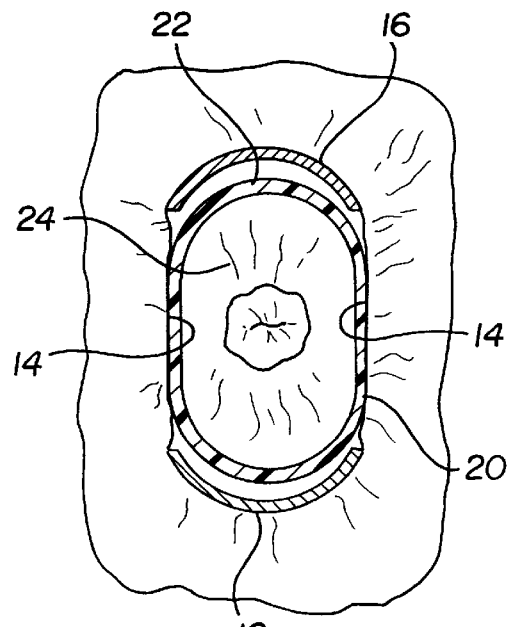
FIG. 3 is a cross-sectional view of the vaginal lateral walls retractor inserted between the opened and inserted blades of the vaginal speculum illustrating the now retracted lateral vaginal walls.

Referring now to FIGS. 1–3 of the drawings in detail, numeral 10 generally indicates a vaginal lateral walls retractor for use with a vaginal speculum 12. The walls retractor 10 eliminates the problems arising when examining women who are obese, elderly, have excess adipose vaginal tissue, or otherwise poorly toned vaginal walls, with a two-bladed speculum 12. Normally, the vaginal walls 14 will push back in under the blades 16 of the speculum 12, obstructing the view of the health care provider and preventing the examination or sampling of the vaginal area as shown in FIG. 2. The present invention allows the health care provider to obtain an unobstructed view and access of the vaginal and cervical areas by retracting lateral vaginal walls 14 as shown in FIG. 3.

The vaginal lateral walls retractor 10 includes a generally tubular sleeve 18. The sleeve 18 illustrated in FIGS. 1–3 is of a generally rectangular or elongated oval shape and has cross-sectional dimensions 20,22 that allow the sleeve 18 to fit between the blades 16 of the speculum 12 while the blades 16 are inserted and opened within the vagina. The configuration of the walls retractor 10 allows it to be used with various sized specula. As the sleeve 18 is being inserted, it retracts the vaginal lateral walls 14 that have been pushed in under the inserted and opened speculum blades 16. The cross-sectional dimensions 20,22 also provide a maximum inside working area 24 for examination and sampling of the vaginal and cervical area. The cross section is preferably of the generally rectangular shape but may also be circular, elliptical (FIGS. 4 and 5) or any combination thereof.

In one embodiment of the present invention, the sleeve 18 has a length that is about 60% of the length of a blade of the speculum and a rectangular shaped cross section as shown in FIG. 1. With the tubular sleeve length at about 60% of the blade length, it is possible to rotate the rectangular sleeve 18 ninety (90) degrees after insertion. Such rotation provides additional lateral wall retraction due to the long dimension of the sleeve 18 being placed horizontally, from vertical; and extending between the lateral vaginal walls.

A handle 26 extends from one end 28 of the sleeve for manipulation by a health care provider such as steering, retaining and positioning the sleeve within the vagina. The handle 26 may have a portion 30 such as a hook that allows the provider to keep the handle 26 to one side of the speculum blades 10 for maximum through clearances for brush, spatula, scraper, external lights, catheter, dilators or other tools used during examination and sampling. The handle 26 has a length that allows full placement of the sleeve 18 down to and around an outer diameter of the ectocervix and allows the sleeve 18 to be pushed toward and away from anterior and posterior vaginal fornix.

Figure 4:
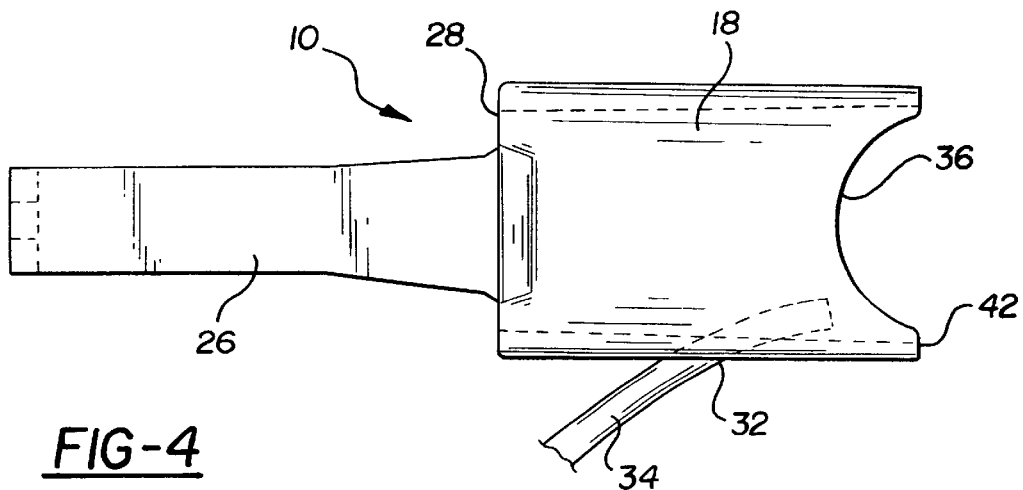
FIG. 4 is a side view of a vaginal lateral walls retractor in accordance with another embodiment of the invention.

Referring to FIG. 3, the inside working area 24 of the sleeve is the space within which the health care provider collects a cervical canal surface sample with the endocervical cytology brush, rotates the ectocervical scraper around the ectocervix for the ectocervical sample, and collects a sample from the posterior vaginal fornix with the spatula end. Having only a partial sleeve length (about 60% of blade length) provides for more maneuverability of the brush and scraper/spatula. Further, the partial sleeve length allows for excellent viewing of the vaginal area. Also, an excellent view of the area is achieved by having a notch 32 in the sleeve 18 to accommodate a light pipe channel 34 on a disposable speculum as shown in FIGS. 4 and 5.

The walls retractor 10 can be used directly or adapted slightly to work with any size or type, metal or plastic speculum. The walls retractor 10 can be made from either metal or plastic.

In a preferable embodiment of the present invention, the lateral walls retractor 10 has a rectangular cross section and may include two cutouts 36 on opposing sides 38,40 at the end opposite of the handle 26 or a proximal end 42 of the sleeve 18 so that an ectocervical scraper lobe will not hit the end of sleeve. The cutouts 36 may be of a generally elliptical shape as shown in FIGS. 4 and 5. Such a configuration may prevent the lobe of the ectocervical scraper from touching the sleeve walls, which may potentially interfere with vaginal wall cells collected for testing. Further, cutting out the end 42 of the sleeve 18 also yields a greater open area around the cervix, simulating the use of two specula, one in the horizontal-lateral direction and the other in the vertical direction. This is especially helpful when it is necessary to view the entire diameter of the cervix of a larger patient which may have up to a four (4) cm (1.6") diameter.

Figure 5:
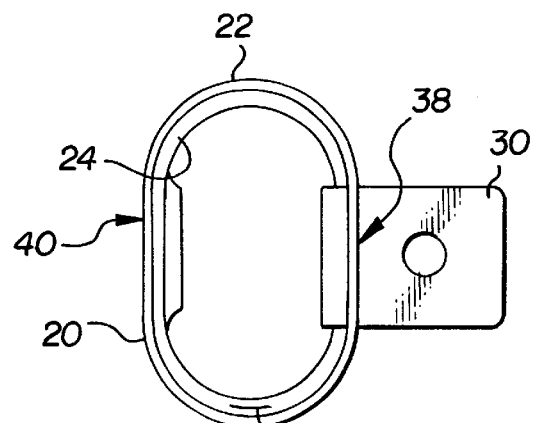
FIG. 5 is an end view of the vaginal lateral walls retractor of FIG. 4.

Referring to FIG. 5, a lip portion 44 may inwardly extend from the side 40 opposite the handle 26 at a distal end 46 of the sleeve 18. The lip portion 44 allows the sleeve 18 to be easily removed from the speculum 12 by preventing the sleeve 18 from getting hung up on a side of the speculum 12 during removal of the sleeve 18.

Figure 6:
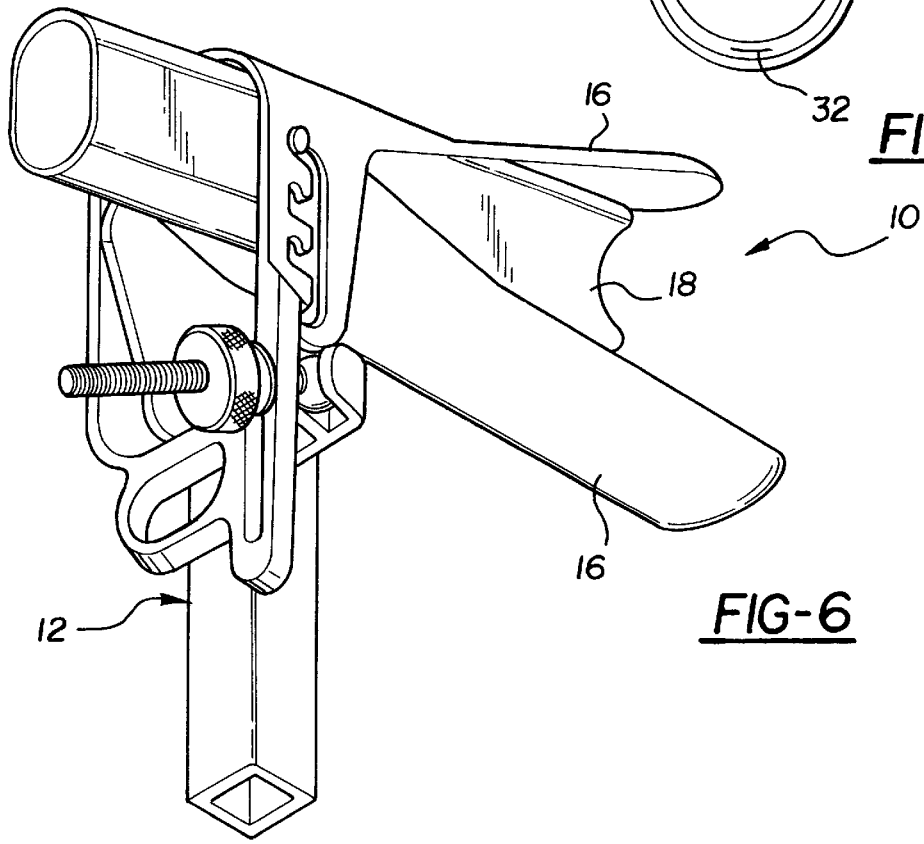
FIG. 6 is a perspective view of a vaginal lateral walls retractor and a vaginal speculum in accordance with another embodiment of the present invention.

In another embodiment, the sleeve length is slightly longer than the speculum blades 16 and extends outside the introitus of the speculum 12 after the sleeve 18 is inserted as shown in FIG. 6. This configuration prevents the sleeve 18 from getting hung up on the introitus yoke of the speculum 12 upon removal of it from the speculum 12, but does not generally allow 90° rotation of sleeve 18.

The present invention also provides a method of performing a vaginal or cervical examination on a patient which includes the following steps. Blades of a conventional vaginal speculum are inserted into the patient's vagina. Once inserted, the blades are opened. Next, a vaginal lateral walls retractor of a generally tubular shape is inserted in between the opened speculum blades for retracting the vaginal lateral walls. To gain additional lateral walls retraction, the vaginal lateral walls retractor tubular shape is generally rectangular in cross section and the larger diameter of the cross section may be rotated 90 degrees to extend between the lateral side walls. Finally, the vagina and cervix area are examined and samples may be taken.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A vaginal lateral walls retractor for use with a vaginal speculum during vaginal/cervical examinations, said wall retractor comprising: a generally tubular sleeve having cross-sectional dimensions that form a generally rectangular shape with rounder corners adapted to fit between the speculum blades while the blades are inserted and opened within a vagina, said sleeve having a length that is greater than the length of the speculum blades such that the sleeve extends beyond an introitus of the vaginal speculum after the sleeve is inserted into the vaginal speculum, said sleeve retracting the vaginal lateral walls that have pushed in under the inserted and opened speculum blades and said sleeve providing an inside working area for examination, therapy and sampling of the vagina and cervix area.

2. A vaginal lateral walls retractor as in claim 1 wherein the sleeve has four sides and two cutouts on opposing sides at a proximal end of the sleeve so that an ectocervical scraper lobe will not hit the end of the sleeve.

3. A vaginal lateral walls retractor as in claim 1 wherein the sleeve has a length that is about 60% of the length of a blade of the speculum.

4. A vaginal lateral walls retractor as in claim 3 further including a handle extending from one end of the sleeve for manipulation by a health care provider.

5. A vaginal lateral walls retractor as in claim 4 wherein the handle has a gripping portion extending generally transverse to the longitudinal direction of said tubular sleeve.

6. A vaginal lateral walls retractor as in claim 4 wherein the handle has a length that allows full placement of the sleeve down to and around an outer diameter of the cervix and allows the sleeve to be pushed toward and away from anterior and posterior vaginal fornix.

7. A vaginal lateral walls retractor as in claim 1 wherein the sleeve is made of a plastic material.

8. A vaginal lateral walls retractor as in claim 1 wherein the sleeve includes a notch to accommodate a light pipe channel on a disposable speculum.

9. A vaginal lateral walls retractor as in claim 1 wherein the cross-sectional dimensions form a generally rectangular shape with rounded corners.

10. A vaginal lateral walls retractor as in claim 9 wherein the sleeve has four sides and two cutouts on opposing sides at a proximal end of the sleeve so that an ectocervical scraper lobe will not hit the end of the sleeve.

11. A vaginal lateral walls retractor as in claim 10 wherein said cutouts are of a generally elliptical shape.

12. A vaginal lateral walls retractor for use with a vaginal speculum during vaginal/cervical examinations, said wall retractor comprising: a generally tubular sleeve adapted to cooperatively fit between the speculum blades while the blades are inserted and opened within a vagina, said sleeve having a length that is about 60% of the length of a blade of the speculum, said sleeve also including a handle extending from one end of the sleeve for manipulation by a health care provider and a lip portion inwardly extending from a distal end of the sleeve, said sleeve retracting the vaginal lateral walls that have pushed in under the inserted and opened speculum blades and said sleeve providing an inside working area for examination, therapy and sampling of the vagina and cervix area.

13. A vaginal lateral walls retractor for use with a vaginal speculum during vaginal/cervical examinations, said wall retractor comprising: a generally tubular sleeve made of a metal material adapted to cooperatively fit between the speculum blades while the blades are inserted and opened within a vagina, said sleeve retracting the vaginal lateral walls that have pushed in under the inserted and opened speculum blades and said sleeve providing an inside working area for examination, therapy and sampling of the vagina and cervix area.

14. A method of performing a vaginal/cervical examination on a patient, said method comprising the steps of:

inserting blades of a vaginal speculum into the patient's vagina;

opening the vaginal speculum blades;

inserting a vaginal lateral walls retractor of a tubular sleeve shape in between the opened speculum blades for retracting the vaginal lateral walls; and examining and collecting samples from the vaginal and cervix area.

15. A method as in claim 14 wherein the vaginal lateral walls retractor has a cross section of a generally rectangular shape.

16. A method as in claim 15 further including the step of rotating the vaginal lateral walls retractor to dispose the larger diameter dimension of the cross section between the lateral vaginal walls thereby gaining additional wall retraction.

\* \* \* \* \*